ARTICLE COMPRISING AN ELASTOMERIC CONTROLLED RELEASE INSECTICIDE

United States Patent [19]
Chapin et al.

[11] Patent Number: 4,767,812
[45] Date of Patent: * Aug. 30, 1988

[54] ARTICLE COMPRISING AN ELASTOMERIC CONTROLLED RELEASE INSECTICIDE

[75] Inventors: John T. Chapin, Alpharetta; Raffaele A. Sabia, Atlanta, both of Ga.

[73] Assignee: American Telephone and Telegraph Company, AT&T Laboratories, Murray Hill, N.J.

[*] Notice: The portion of the term of this patent subsequent to Jun. 10, 2003 has been disclaimed.

[21] Appl. No.: 856,183

[22] Filed: Apr. 28, 1986

Related U.S. Application Data

[63] Continuation-in-part of Ser. No. 729,267, May 1, 1985, Pat. No. 4,594,380.

[51] Int. Cl.$^4$ .............................................. C08L 75/04
[52] U.S. Cl. .................................. 524/144; 523/102; 523/122; 528/75
[58] Field of Search ................ 524/144, 712; 523/102, 523/122; 528/75

[56] References Cited
U.S. PATENT DOCUMENTS
4,594,380  6/1986  Chapin et al. ........................ 524/144

Primary Examiner—Maurice J. Welsh
Attorney, Agent, or Firm—Eugen E. Pacher

[57] ABSTRACT

An article for the sustained release of an insecticide into the ambient air comprises an elastomeric matrix, with the insecticide dissolved in the matrix. The matrix material has a modulus between about $10^4$ Pa and about $10^8$ Pa at 23° C., and a glass transition temperature less than 0° C. The matrix comprises polyurethane formed by reacting hydroxyl-terminated polybutadiene or polyisoprene and 4,4' diphenylmethane diisocyanate, and the insecticide is 2,2' dichlorovinyl dimethyl phosphate. The insecticide-containing matrix is contained in a plastic bottle, and typically protected against inadvertent skin contact by means of a dermal barrier. The article also comprises means for activating the article such that, prior to activation, release of insecticide into the ambient air is prevented, whereas such release can take place after activation. Exemplary activation means comprise a metal foil seal of the plastic bottle. The article is effective in controlling insect infestation (e.g., ants, fire ants, bees, wasps, cockroaches) in enclosures, e.g., enclosures of the type used to protect outdoor utility equipment.

7 Claims, 4 Drawing Sheets

ARTICLE COMPRISING AN ELASTOMERIC CONTROLLED RELEASE INSECTICIDE

CROSS REFERENCE TO RELATED APPLICATION

This application is a continuation-in-part of U.S. patent application, Ser. No. 729,267, filed May 1, 1985 and now U.S. Pat. No. 4,594,380.

FIELD OF THE INVENTION

This invention pertains to means for the sustained release of an active agent into the environment. In particular, the invention pertains to means comprising a polyurethane elastomeric matrix in which the active agent is contained, typically dissolved.

BACKGROUND OF THE INVENTION

The need for the controlled and sustained release of an active agent into the environment exists in many fields, for instance, in residential and other consumer fields, in agriculture, and in telecommunications and other areas of technology, and the prior art knows a variety of methods for achieving such release.

One class of methods comprises dispersion of the active agent throughout (or dissolution in) a substantially inert matrix from which the active agent is gradually released into the environment. The discussion herein will be limited to controlled-release methods of this type, and to devices using this method. Such devices are frequently referred to as "monolithic" devices.

Matrices that have been used in monolithic devices include plasticized polyvinylchloride, rubbers, (see, for instance, U.S. Pat. No. 3,318,269) and some polyurethanes. Prior art rubber matrices typically are cured by conventional rubber chemistry, e.g., by sulfur vulcanization or by means of peroxides. See, for instance, U.S. Pat. No. 3,639,583. These curing processes typically comprise a high-temperature step, i.e., a process step during which the matrix material with the active agent therein is heated to a temperature above about 100° C., frequently even to a substantially higher temperature.

A prior art example of the use of a polyurethane matrix can be found in U.S. Pat. No. 4,189,467 ('467), incorporated herein by reference, which discloses a plastic composition comprising polyurethane. The matrices disclosed in the above patent typically are relatively nonelastomeric, due to the inclusion of filler materials, use of low molecular weight (30–400) reactive materials (e.g., butane diol) and/or to the choice of low molecular weight polyols and low molecular weight isocyanates. For instance, in an exemplary composition the patent discloses the use of about 43 parts of filler material, with the polyurethane formed by the reaction of relatively low molecular weight polyols and isocyanates, resulting in a relatively high modulus polyurethane requiring the use of a plasticizer to reduce the stiffness of the composition. A further possible reason for the frequent use of a plasticizer in the prior art composition is the facilitation of the migration of the active agent through the relatively impermeable matrix to the release surface.

U.S. Pat. No. 4,094,970 discloses that elastomeric materials, specifically, matrices formed from a polyisocyanate and units of a long chain polyol (having a molecular weight from 1000 to 10,000) and at least one of a short chain polyol and/or polyamine (having a molecular weight of 62 to 1,000), can advantageously be used as matrices for insecticidal active compounds. Such mixtures typically require high isocyanate content, resulting in a relatively stiff matrix. Use of polyamines in high isocyanate formulations further increases the stiffness of the matrix. Furthermore, such formulations tend to have high exotherms during reaction.

Many of the prior art controlled release systems of the type discussed herein require a high temperature processing step. Such a step frequently is a complicating factor when active agents having relatively high vapor pressure, or active agents that are subject to deactivation at the elevated temperature, are to be incorporated into the matrix material.

Some prior art controlled release systems require the use of a carrier substance, frequently a plasticizer, to at least assist in the transport of the active agent to the release surface. Such systems are often subject to deposition of active agent on the release surface (blooming). However, blooming can also be due to the properties of the active agent, and may be desired at times. Use of a carrier substance may also lead to incomplete release of active agent. The latter shortcoming is typically due to an increase in the glass transition temperature of the matrix with increasing plasticizer loss, resulting in a decreasing release rate and eventual virtual cessation of release, frequently with a substantial amount of active agent still present in the matrix. Such behavior leads to unnecessarily shortened product life.

Because of the importance of controlled release of active agents, a controlled release system that does not have some of the shortcomings of prior art systems, e.g., that is free of high temperature reaction or processing steps, that is resistant to hydrolysis and water uptake, is not subject to syneresis, that has the potential for release of a high proportion of the active agent, and that furthermore has wide applicability, would be of substantial benefit. This application discloses such a system.

GLOSSARY OF TERMS

A "matrix" herein is the elastomeric material formed by a crosslinked polymer, possibly containing such property-modifying agents as fillers, plasticizers, stabilizers, fungicides, pigments, and the like.

By "elastomer" we mean herein an amorphous crosslinked polymer material having a glass transition temperature $T_g$ less than about 0° C., and a tensile modulus in the range from $10^4$ to $10^8$ Pa at 23° C.

Figure 1:
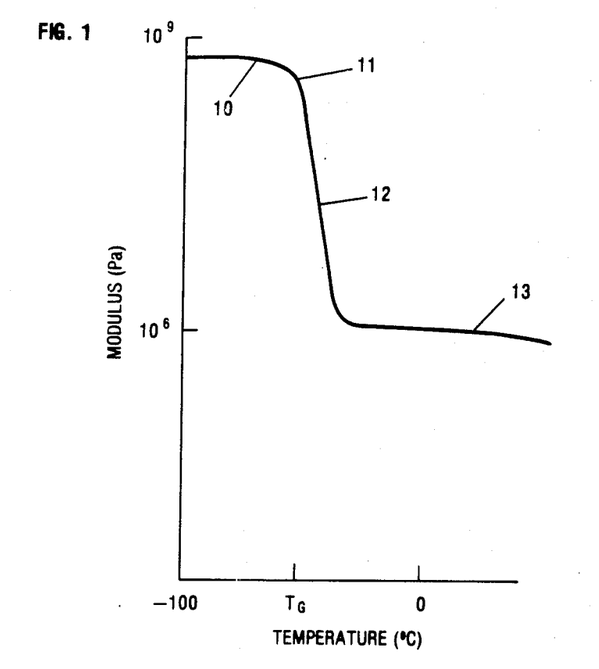
FIG. 1 shows in generalized form the modulus, as a function of temperature, of a material that is an elastomer in the temperature range of interest herein.

The "glass transition temperature" of a material is the temperature, determined, for instance, by means of stress/strain measurement, at which the modulus of the material changes from a relatively high value obtaining in the (low temperature) "glassy" state of the material to the lower value obtaining in the transition region to the (higher temperature) "rubbery" state of the material. This is illustrated in FIG. 1.

A "polyol" herein is a higher molecular weight (400–10,000) compound containing at least two groups which are reactive with isocyanates.

An "isocyanate" herein is a compound having two or more endgroups of the type $-N=C=O$.

A "prepolymer" is an adduct or reaction intermediate of polyol and isocyanate, in which the NCO/OH ratio is at least about 1.5.

Unless defined differently herein, all chemical terms are intended to have their customary meaning, as defined, for instance, in *The Condensed Chemical Dictio-*

SUMMARY OF THE INVENTION

An article according to the invention comprises an elastomeric matrix and, contained in the matrix material, one or more active agents, the active agent(s) to be released into the environment substantially continuously over an extended period of time. The matrix material comprises a polyurethane elastomer having a modulus between about $10^4$ and about $10^8$ Pa at 23° C., and a glass transition temperature $T_g$ less than 0° C.

The polyurethane elastomer is formed by a process comprising reacting polyol with isocyanate. The polyol comprises a major component, and, optionally, a minor component. The major component typically makes up at least 90% by weight of the polyol and is selected from the group consisting of hydroxyl-terminated compounds selected from the group consisting of polybutadiene, polyisoprene, copolymers of butadiene with acrylonitrile, copolymers of butadiene with styrene, copolymers of isoprene with acrylonitrile, copolymers of isoprene with styrene, and mixtures of two or more of the above. The optional minor component is selected from the group consisting of carboxyl-terminated compounds selected from the group consisting of polybutadiene, polyisoprene, copolymers of butadiene with acrylonitrile, copolymers of butadiene with styrene, copolymers of isoprene with acrylonitrile, copolymers of isoprene with styrene, and mixtures of two or more of the above. The polyol has an average molecular weight in the range 400–10,000.

The isocyanate is selected from the group consisting of the aromatic, cycloaliphatic, aliphatic and heterocyclic isocyanates, and mixtures of two or more of the above. The isocyanate has an average molecular weight in the approximate range 80–1,000, and an average functionality between about 2 and about 3, with the NCO/OH ratio of the isocyanate and the polyol being in the range 0.8 to 1.2.

The matrix optionally may comprise components that do not participate in the urethane-forming reaction between polyol and isocyanate. Among such "nonreactive" components are fillers, plasticizers, stabilizers, pigments, and fungicides. The total amount of nonreactive components of the matrix is at most 50% by weight of the matrix, with the amount of nonreactive component exclusive of fillers and plasticizers being typically at most about 5% by weight of the matrix.

Contained in the matrix is the material to be controllably released into the ambient environment, collectively referred to as the active agent.

The matrix material has a low curing exotherm and typically has a lower modulus than prior art controlled release matrices. We believe that the latter is associated with improved (e.g., more complete) release of the active agent into the environment. For instance, we observe that in typical combinations according to the invention more than 70, 80, or 90% of the total amount of active agent in the matrix is released into the environment. Furthermore, matrices according to the invention typically are highly hydrophobic, making possible the use, even in humid or aqueous environments, of active agents that are subject to hydrolysis.

The active agent can be substantially any biologically or nonbiologically active compound that is compatible with the matrix material. Exemplary classes of possible active agent compounds are the aliphatic or aromatic oils, esters (phosphorous, sulfurous, or hydrocarbon-type), ketones, ethers, halogenated aromatic compounds, and organometallics. In preferred embodiments the active agent is dissolved in the matrix, with the release mechanism comprising diffusion of active agent from the interior of the sample to the release surface.

The inventive combination (matrix plus active agent) can be formed into a variety of shapes, combined, if desired, with appropriate containment means, to form an article providing timed-release biological or nonbiological action, e.g., insecticidal, fungicidal, deodorant, molluscicidal, anti-corrosive or anti-static action.

DETAILED DESCRIPTION

An important aspect of the invention is the use of a highly elastomeric matrix. In particular, we have discovered that use of an elastomeric matrix of relatively low modulus can result in improved release characteristics. Among the improved characteristics is more complete release of active agent. The amount released can be as high as 70, 80, or even 90% of the total amount of active agent in the matrix.

The elastomeric nature of the matrix results in a volume change of the matrix as active material is lost therefrom. By this process, the matrix maintains its overall nature. Furthermore, the nature of the matrix allows substantial shrinkage of the matrix without cracking and/or pore or void formation. It is obvious that cracking or pore formation would be undesirable in many applications, due to the loss of mechanical integrity or due to the possibility of water absorption into the material. A further possible deleterious effect of pore formation is collection of active agent in pores, which might result in a change in release behavior. Use of an elastomeric matrix according to the invention typically also results in lower temperature sensitivity of the release behavior, as compared to at least some prior art matrices, e.g., plasticized PVC (polyvinylchloride) matrices.

A further important aspect of the invention is the relatively low heat of reaction during formation of matrices according to the invention. This in turn prevents substantial heating of the material during the urethane-forming reaction and thus avoids the above-mentioned high temperature related problems associated with some prior art materials. It will be understood by those skilled in the art that the temperature rise of a given quantity of polyurethane-forming mixture depends, inter alia, on the geometry, quantity, and cure rate of the reacting mixture. In exemplary cases we have found, however, that the temperature rise during the reaction of a sample of inventive material typically is less than 40° C., and frequently as low as 20° or 10° C. (for 100 gm of material in ambient air).

Matrices according to the invention contain polyurethane as a major component. The matrix is formed from a matrix-forming mixture comprising polyol, or a mixture of polyols. While polyols containing carboxyl groups may be present as an optional minor component of the polyol, hydroxyl-terminated polyols constitute the major part of the polyol. The hydroxyl groups can be either primary, secondary, or tertiary, with the reactivity of the polyol depending on the nature of the group, as is well known to those skilled in the art. Typically, hydroxyl-terminated polyols useful in the practice of the invention are mixtures of diols and triols, having an average functionality in the range from about 2.0 to about 2.8, and having a molecular weight in the range from about 400 to about 10,000, preferably 1,000–4,000. As is also well known to those skilled in the art, higher molecular weight polyols yield a lower crosslink density, at a given functionality, than those of lower molecular weight. Lower crosslink density facilitates release of the active agent from the matrix in controlled release systems according to the invention, and therefore is typically a desirable property.

Among currently preferred hydroxyl-terminated polyols are polyols having a molecular weight of about 2800 and an average functionality of typically about 2.4–2.6. A polyol having these characteristics is available from ARCO Chemical Company of Philadelphia, Pa. under the trade designation POLY BD R-45HT.

Typically, the compatibility of the active agent with the polyol is a significant consideration in the formulation of the system. In order to improve the compatibility, it may in some cases be advantageous to use a mixture of polyols, including a polyol that is relatively more compatible with the active agent. For instance, if the active agent is a relatively nonpolar, e.g., aliphatic, molecule then the compatibility may be improved by the addition of a (nonpolar) aliphatic polyol. Examples of such polyols are castor oil and a monofunctional alcohol available from Henkel Corp., Hoboken, N.J., under the trade designation Primarol 1511. The former typically should be at most 10% b.w., the latter typically at most 2% b.w., of the polyol. The polyol component of the polyurethane-forming mixture may also contain acrylonitrile/butadiene copolymers, such as a material available from ARCO Chemical under the trade designation CN-15. Such copolymers typically are polar materials and can, therefore, be used to improve the compatibility of the matrix with polar active agents. Other polyols (e.g., styrene-butadiene copolymers available from ARCO Chemical under the trade designation CS-15) could sometimes also be added to alter one or more material properties of the matrix material, e.g., the glass transition temperature. For instance, use of a triol typically increases the crosslinking density, and therefore the modulus. A minor amount of carboxylic acid-terminated polyols could be used.

Isocyanates that can be used in the practice of the invention include essentially any of the known aliphatic, cycloaliphatic, aromatic, and heterocyclic polyisocyanates, such as are described, for instance in Chapter V, especially Tables 1–16, of J. K. Stille and T. W. Campbell, *Condensation Monomers*, J. Wiley and Sons (1972). The chemistry and nature of polyols and isocyanates are well known to those skilled in the art.

Currently preferred isocyanates are polyarylene polyisocyanates. These aromatic compounds tend to be polar, and therefore are especially useful in conjunction with polar active agents. Examples of such aromatic isocyanates are 2,4 toluene diisocyanate, and 2,6 toluene diisocyanate, mixtures thereof, and 4,4' diphenylmethane diisocyanate and its oligomers. The latter are available, for instance, from Upjohn Polymer Chemicals of LaPorte, Tex. under the trade designation PAPI. For systems according to the invention that comprise less polar or nonpolar active agents, it may be advantageous to use aliphatic isocyanates, e.g., 1,6 hexamethylene diisocyanate. This material is available from Mobay Chemical Company of Pittsburgh, Pa. under the trade designation Mondur HX. For the same reason, it may in some cases be useful to incorporate 3,5,5 trimethylcyclohexyl isocyanate (IPDI) (available from Chemische Werke Huls, AG, F. R. Germany), or 4,4' methylene bis(cyclohexyl isocyanate).

Isocyanates useful in the practice of the invention typically have average functionality between about 2 and 3. Among the currently preferred isocyanates are compounds having an average functionality of about 2.3. The molecular weight of useful isocyanates typically is greater than about 80 and typically less than about 1000, preferably in the range from about 260 to about 400.

For some purposes, it may be advantageous to use a prepolymer. For instance, such a prepolymer is available from Upjohn Polymer Chemicals, under the trade designation Isonate 181. Such prepolymerization typically reduces the vapor pressure of isocyanate, and therefore may be useful for, inter alia, environmental or health reasons. Furthermore, prepolymerization is useful in the preparation of segmented polyurethanes, e.g., polyurethanes comprising both stiff and flexible molecular segments.

As is well known to those skilled in the art, the properties of a polyurethane depend at least to some extent on the ratio of the equivalent weight of isocyanate to the equivalent weight of polyol, usually expressed in terms of a NCO/OH ratio. For instance, if the ratio is greater than 1 (NCO-rich) then the polyurethane tends to be more rigid, whereas for a ratio less than 1 (OH-rich) the polyurethane tends to be more flexible, with the OH pendent groups acting as internal plasticizers. Understanding that the appropriate value of the NCO/OH ratio depends also on the functionality of the reactive components, we currently consider the range of ratios from about 0.8 to about 1.2 to be a useful one, with currently preferred values lying between about 0.95 and 1.1.

The practitioner also knows that polyurethane polymerization can proceed with or without a catalyst. The purpose of the catalyst is to increase the rate of reaction and thus decrease the gel time. Among catalysts useful in the practice of the invention are tertiary amines, and organometallic compounds. For a listing of exemplary catalysts see, for instance, '467. Exemplary preferred amine catalysts are triethylamine, benzyldimethylamine, and triethylene diamine (DABCO). Among preferred organometallic catalysts are dibutyltin dilaurate and dibutyltin bis isooctyl malleate (both available from M & T Chemicals Co., Rahway, N.J., under the trade designation catalyst T-12 and catalyst 125, respectively) and dioctyltin diricinoleate, available from Caschem, Inc., of Bayonne, N.J. Typical ranges of catalyst concentration in the polyurethane-forming mixture are from about 0.001 to about 2% by weight, preferably 0.01–0.5%.

Although systems according to the invention can comprise any active agent that is compatible with the matrix material, they frequently comprise active agents having a relatively high vapor pressure, typically above about $10^{-4}$ Torr at room temperature (about 23° C.). As was discussed above, incorporation of such active agents into prior art matrices frequently is not completely satisfactory, as high preparative temperatures may be encountered, whereas their incorporation into a matrix according to the invention typically can be accomplished, due to the low exotherm, without substantial loss or deactivation. Of course, low vapor pressure active agents can also be incorporated into inventive matrices, and such combinations may also have advantages over prior art formulations. For instance, such combinations typically can function without the presence of a plasticizer. A possible use for a system according to the invention comprising low vapor pressure active agent is for release of the agent into a liquid medium, e.g., water.

By "compatibility" we mean herein the absence of phase separation (manifested, for instance, by the appearance of cloudiness in the cured state) or reaction between the active agent and any of the constituents of the matrix (or matrix-forming constituents). For instance, active agents that contain an acidic hydrogen typically react with isocyanates, and therefore typically are not compatible with the matrix material. Active agents undergoing reactions with a matrix component are known to the prior art. See U.S. Pat. No. 4,267,281. However, due to the strongly hydrophobic nature of matrices according to the invention, reactive active agents would remain bound to the matrix in systems according to the invention, and therefore currently are not considered to form a useful combination.

Active agents may be biologically active agents such as pesticides, insecticides, molluscicides, parasiticides, deodorants, air fresheners, perfumes, fungicides, repellents, acaricides, fungistats, bioregulators, and medicinally active agents, or they may be nonbiologically active agents such as corrosion inhibitors or agents that reduce or prevent the build-up of static electricity (antistats). Typically, the active ingredient is homogeneously distributed throughout the matrix. However, in some cases it may be advantageous for the active agent to be colloidally dispersed in the matrix, e.g., by use of fumed hydrophilic or hydrophobic silica.

Exemplary active agent types are aliphatic or aromatic oils, esters (phosphorous, sulfurous, or hydrocarbon-type), ketones, ethers, halogenated aromatic compounds, and organometallics such as organic tin or copper compounds.

The class of active agents that are potentially compatible with matrices according to the invention is clearly substantial, and no effort will be made herein to list the members of the class. However, a minor amount of experimentation typically suffices to reveal whether a specific compound is compatible with the matrix material. In general, we are contemplating the use of any compatible active agent in systems according to the invention.

Exemplary active ingredients that we have found to be compatible with a matrix according to the invention are the insecticide 2,2' dichlorovinyl dimethyl phosphate (DDVP, available commercially from SDS Biotech, Inc., Cleveland, Ohio, under the trade name VAPONA), the repellents N,N' diethyl toluamide (DEET) and dimethyl phthalate (DMP), the insecticide and deodorant limonene (dipentene), the pesticide O,O-dimethyl dithiophosphate of diethyl mercaptosuccinate (also known as Malathion), N-mercaptomethyl phthalate S(O,O-dimethyl phosphorothioate), and pyrethrins, the insecticidal components of flowers from chrysanthemum cinerariaefolium.

Controlled release systems according to the invention can be formed by known processes. See, for instance, '467. Typically, they are formed by adding the active agent, or agents, to a quantity of polyol (with possibly a catalyst being present in the polyol), and sufficiently dispersing the active agent to form a substantially homogeneous mixture. To the thus formed mixture isocyanate is added, properly mixed, and the resulting liquid processed into the desired shape, e.g., filled into a container, cast into sheet form, or otherwise shaped by known means. Depending on the amount of catalyst present in the liquid, the nature of the polyol and of the isocyanate used, the reaction between the ingredients proceeds and results in the formation of polyurethane.

The above-described batch processing method for forming the inventive composition is of course not the only possible one, and it is possible to form the composition by a continuous (in-line) process. In such a case, typically the catalyst concentration will be higher than in a batch process, to result in a relatively shorter reaction time.

Although not so limited, in systems according to the invention the transport of active agent to the release surface typically is by means of diffusion through the matrix. As is well known, the diffusion rate inversely depends, inter alia, on the crosslinking density of the matrix. If the vapor pressure of the active agent is sufficiently high, e.g., between about $10^{-4}$ and 1 Torr at room temperature, release into the ambient atmosphere takes place upon arrival of active agent material at the release surface. Some active ingredients of relatively low vapor pressure (typically less than $10^{-4}$ Torr at room temperature) may accumulate at the release surface, and be introduced into the ambient either by sublimation, dissolution or by means of contact with a biological carrier, e.g., an insect.

An important aspect of the invention is the requirement that the elastomeric matrix material have a glass transition temperature $T_g < 0°$ C. This property makes it possible for combinations according to the invention to release significant quantities of active agent at all temperatures of interest, e.g., at those temperatures at which insects such as wasps, fire ants, or cockroaches are active.

FIG. 1 schematically illustrates the general behavior of the modulus of appropriate polymeric material as a function of temperature. A polymer is said to be in the "glassy" state if it is in region 10 of the curve, in which the modulus is high (of order $10^9$ Pa) and substantially constant. The knee 11 in the curve defines $T_g$ and separates the "glassy" region from the transition region 12. Region 13, in which the modulus is low (e.g., of order $10^6$ Pa) and substantially constant, is the elastomeric regime of the polymer.

Another important aspect of the invention is the relatively low modulus of the matrix material, between about $10^4$ and $10^8$ Pa, preferably between $10^5$ and $10^7$ Pa, at 23° C. The lower limit is determined by the requirement that the matrix have sufficient tear strength and substantially retain its shape. The upper limit is determined by the requirement that the material have a $T_g < 0°$ C. Furthermore, we currently believe that elastomeric matrix material with a relatively low room temperature modulus can have higher release rate of active agents than do matrices with higher modulus. A possible explanation for this is the known fact that the former materials have a larger free volume than the latter, resulting in greater ease of migration of active agent molecules in the former.

An elastomeric matrix as disclosed herein will undergo shrinkage as active agent is lost therefrom. We consider this characteristic of the inventive system to be another significant aspect of the invention, since it can facilitate nearly total (more than 50%, preferably more than 70, 80, or 90%) release of active agent from the matrix. We believe that this high release is due at least in part to the relatively low $T_g$ of elastomers of the type described herein, and the relative constancy of $T_g$ throughout the release period.

These characteristics are to be contrasted with those of prior art systems that rely on the use of plasticizers to facilitate the release of the active agent from the matrix. In such prior art systems, $T_g$ tends to increase with increasing loss of plasticizer from the matrix, resulting in decreasing mobility of the active agent with, frequently, virtual cessation of release after release of only a relatively small fraction of the active agent present in the matrix.

The practitioner is familiar with the fact that the amount of active agent released from a controlled release matrix within a given period of time depends, inter alia, on the geometry of the matrix. In particular, it depends on the surface to volume ratio of the sample, with high ratios producing relatively high release rates, whereas low ratios lead to relatively low rates. For instance, a slab-like sample has a relatively high surface/volume ratio, and a cylinder or sphere has a relatively low ratio. Depending on the envisaged application, either high ratio or low ratio geometries may be appropriate, and we envisage all possible geometries as being within the scope of this application. For instance, for some insecticidal applications, we have found a low surface to volume ratio geometry appropriate, such as is obtained by filling the active agent-containing matrix material into a low permeability bottle. On the other hand, for air freshener applications, we have found a high surface to volume ratio geometry, such as is obtained with a wafer, to be advantageous.

Figure 2:
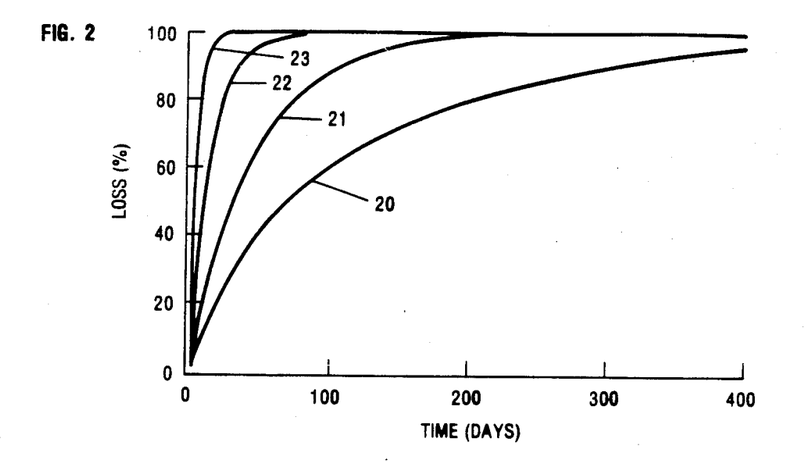
FIGS. 2–4 show exemplary active agent release data.

FIG. 2 shows exemplary data on weight of active agent (VAPONA) lost from a slab-like sample (for composition, see Example 1) according to the invention versus time. The samples were disks having a diameter of about 51 mm and a thickness of about 4.6 mm. Curves 20-23 show data for 23°, 40°, 50°, and 65° C., respectively.

The measured data can be fitted by expressions of the form:

$$\% \text{ loss} = b_o + b_1 t \text{ (for loss } <30\%)$$

and $$\% \text{ loss} = 100 - \exp(b_o + b_1 t) \text{ (for loss } >30\%)$$

where t=time, and $b_o$ and $b_1$ are constants whose values depend, inter alia, on temperature and geometry. As is well known, functional dependency of this form implies transport-limited release.

Figure 3:
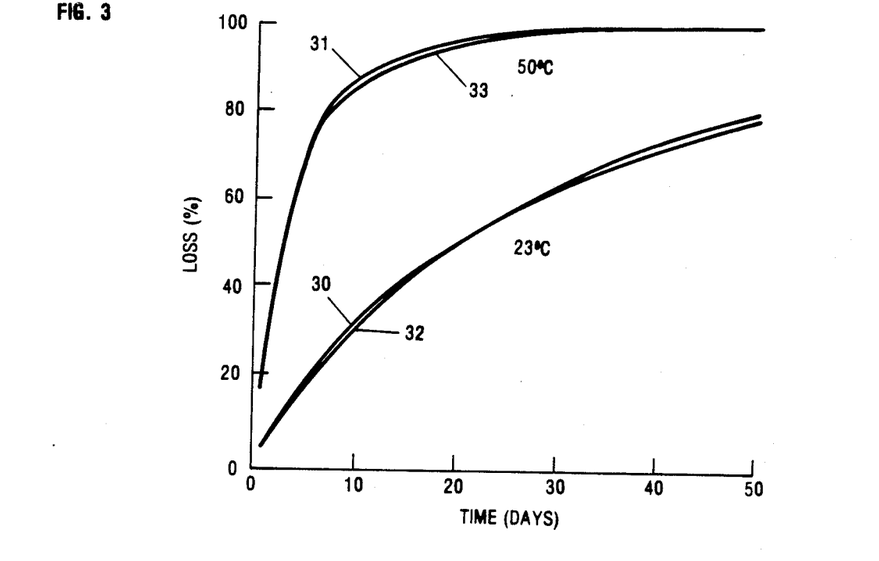

FIG. 3 exemplifies the release behavior of a combination according to the invention, with the samples having the previously described wafer geometry. Two samples (curves 30 and 31) have a composition substantially as described in Example 1 below, (except that they contained 28.5% by weight VAPONA) and two samples (32 and 33) being produced from material of the same composition as used for 30 and 31, but containing 20% by weight filler ($Al_2O_3 3H_2O$ particles about 16 $\mu$m size). Curves 31 and 33 were obtained at 50° C., curves 30 and 32 at room temperature. At 50° C. more than 90% of the active agent was released during the time of the experiment. Although only about 45% of the active ingredient was released during the same time at 23° C., it is known from other experiments that ultimately more than 80% will be released from a sample of this type.

Figure 4:
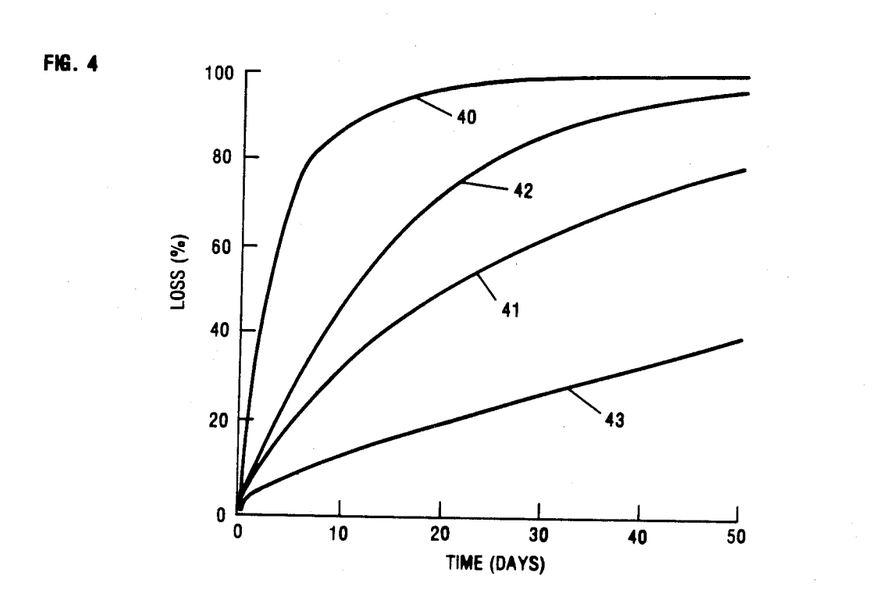

FIG. 4 exemplifies the effect of packaging on release rate. Curves 40 and 41 were obtained with a wafer sample as described, with all of the sample surface exposed to the ambient, and curves 42 and 43 with the same type of sample packaged in a plastic container and supported therein on prismatic edges, the container having a 950 mm$^2$ opening. Curves 40 and 42 were obtained at 50° C., and 41 and 43 at 23° C.

We will next describe an exemplary preparation of an article according to the invention. It will be understood that other preparation schemes are possible and are known.

EXAMPLE 1

Into a 10 liter closed reaction vessel equipped with mechanical stirrers and means for $N_2$ purging, the following were introduced at room temperature: 71.6 parts of hydroxyl-terminated polybutadiene (Poly BD, R-45HT), 20.0 parts 2,2-dichlorovinyl dimethyl phosphate (VAPONA, at least 93.1% pure) and 0.3 parts dibutyltin dilaurate (T-12). After stirring for about 5 minutes, which produced essentially complete homogenization, 8.1 parts polymethylene-polyphenyl isocyanate (PAPI 94) was added, and the mixture stirred again for about 5 minutes. About 100 cc of the mixture was poured into a 120 cc plastic bottle, a further part of the mixture was poured onto a plastic-lined tray, where it formed a slab of approximately 4 mm thickness. The gel time of the mixture was about 30 minutes. The temperature of neither sample rose by more than 10° C. during the reaction.

The resulting material was dry, amber colored, and had a modulus of about $10^6$ Pa at 23° C., and a $T_g$ of about −75° C. (as determined by DSC). A similarly prepared polyurethane sample that did not contain any active agent had substantially the same $T_g$.

EXAMPLE 2

Samples were prepared substantially as described in Example 1, except that 28.5 parts of VAPONA was used (71.2 parts polyurethane). No significant difference in reaction rate, exotherm, appearance and $T_g$ was observed. The modulus was about $5 \cdot 10^5$ Pa at 23° C.

EXAMPLE 3

Samples were prepared substantially as described in Example 1, except that 30 parts of polyurethane were replaced by 30 parts of $Al_2O_3 3H_2O$ powder (about 16 $\mu$m particle size). The only significant change was in the color of the sample, being white rather than amber.

EXAMPLES 14-16

The samples are prepared substantially as described in Example 1, with the indicated active ingredient being substituted, where appropriate, for VAPONA. All of the matrices of Examples 4-16 have room temperature moduli between $10^5$ and $10^7$ Pa, have $T_g < 0$° C., and release rates qualitatively similar to those shown in FIG. 2. The compositions are summarized in Table I.

TABLE I

| Example No. | Active Agent Type | Matrix Parts | Composition |
|---|---|---|---|
| 4 | A | 20 | M |
| 5 | A | 20 | N |
| 6 | A | 20 | O |
| 7 | B | 20 | P |
| 8 | C | 20 | P |
| 9 | D | 20 | P |
| 10 | E | 20 | P |
| 11 | F | 20 | P |
| 12 | G | 20 | P |
| 13 | H | 20 | P |
| 14 | J | 20 | P |
| 15 | K | 20 | P |
| 16 | L | 20 | P |

Key to Table I:
A: VAPONA, (insecticide);
B: Limonene, (insecticide, boiling point (B.P.) 175–177° C.);
C: Diazinon, (insecticide, B.P. 83–84° C., vapor pressure (V.P.) 2 $10^{-3}$ mm Hg at 20° C.);
D: Malathion, (insecticide, B.P. 156–157° C., V.P. 4 $10^{-5}$ mm Hg at 30° C.);
E: Methylnonyl ketone, (repellent, B.P. 231–232° C.);
F: Cis, 7, 8-epoxy-2-methyl octadecane (attractant);
G: p-propenyl anisole (attractant, B.P. 234–237° C.);
H: 1, 2 dibromo-3-chloropropane (nematocide, B.P. 195° C., V.P. 8 $10^{-1}$ mm Hg at 25° C.);
J: Carbontetrachloride (fungicide, B.P. 77° C., V.P. 114 mm Hg at 25° C.);
K: Methyloctonate and methyldecanoate (growth regulator, B.P. 194–195° C.);
L: 2, chloro-6-trichloromethyl pyridine (bactericide, M.P. 62–63° C., V.P. 2.8 $10^{-3}$ mm Hg at 23° C.);
M: 68.8 parts R-45HT (equivalent weight (E.W.) 1,205),
  11.0 parts Isonate 181 (E.W. 183),
  0.2 parts T-12,
  NCO/OH = 1.5;
N: 51.4 parts R-45 HT,
  20.6 parts CS-15 (E.W. 1534),
  7.7 parts PAPI 94 (E.W. 133),
  0.3 parts T-12,
  NCO/OH = 1.05,
O: 73.6 parts CN-15 (E.W. 1,666),
  6.2 parts PAPI 94,
  0.2 parts T-12,
  NCO/OH = 1.05,
P: 71.7 parts R-45 HT (E.W. 1,205),
  8.1 parts PAPI 94
  0.2 parts T-12,
  NCO/OH = 1.02.

Chemical name and source of substances listed by trade name were previously identified.

EXAMPLES 17–22

The samples are prepared substantially as described in Example 1, with the indicated urethane-forming components. All of the matrices of Examples 17–22 have room temperature moduli between $10^5$ and $10^7$ Pa, have $T_g < 10°$ C., and VAPONA release rates qualitatively similar to those shown in FIG. 2. The compositions are summarized in Table II. The NCO/OH ratio of the compositions is about 1.05.

TABLE II

| Example No. | Active Agent Type | Active Agent Parts | Polyol Type | Polyol Parts | Isocyanate Type | Isocyanate Parts | Catalyst Type | Catalyst Parts | Additional Matrix Components Type | Additional Matrix Components Parts |
|---|---|---|---|---|---|---|---|---|---|---|
| 17 | A | 20 | Q | 72.6 | T | 7.1 | W | 0.3 | | |
| 18 | A | 20 | Q | 66.1 | U | 10.8 | W | 0.3 | | |
|   |   |   | R | 2.8 |   |   |   |   | | |
| 19 | A | 20 | Q | 74.3 | V | 5.4 | W | 0.3 | | |
| 20 | A | 20 | Q | 56.2 | U | 11.5 | W | 0.3 | | |
|   |   |   | S | 12.0 |   |   |   |   | | |
| 21 | A | 20 | Q | 71.5 | U | 8.1 | W | 0.3 | X | 0.1 |
| 22 | A | 20 | Q | 71.4 | U | 8.1 | W | 0.3 | Y | 0.2 |

Key to Table II
A: VAPONA
Q: R-45HT
R: Primarol 1511 (E.W. 125)
S: Castor Oil (E.W. 342)
T: IPDI (E.W. 111)
U: PAPI 94
V: MONDUR HX (E.W. 84)
W: T-12
X: IRGANOX 1076 (octadecyl 3-(3′,5′-di-tert-butyl-4′-hydroxyphenyl)propionate), an antioxidant available from Ciba-Geigy Corp., of Ardsley, New York
Y: METASOL TK 100 (2-(-4 thiazol) benzimidazole), a fungicide available from Calgon Corp., Pittsburgh, Pa.

A currently preferred embodiment comprises about 70–90% polyurethane and 10–30% active ingredient, with the polyurethane formed from about 5–15% isocyanate (typically 4,4′-diphenylmethane diisocyanate, or oligomers thereof) and about 55–85% polyol (typically a hydroxyl-terminated polybutadiene having an average M.W. 1000–4000 and an average functionality 2.4–2.6), all percentages being weight percent of the total formulation. An advantageous active ingredient comprises 2,2′ dichlorovinyl dimethyl phosphate.

Figure 5:
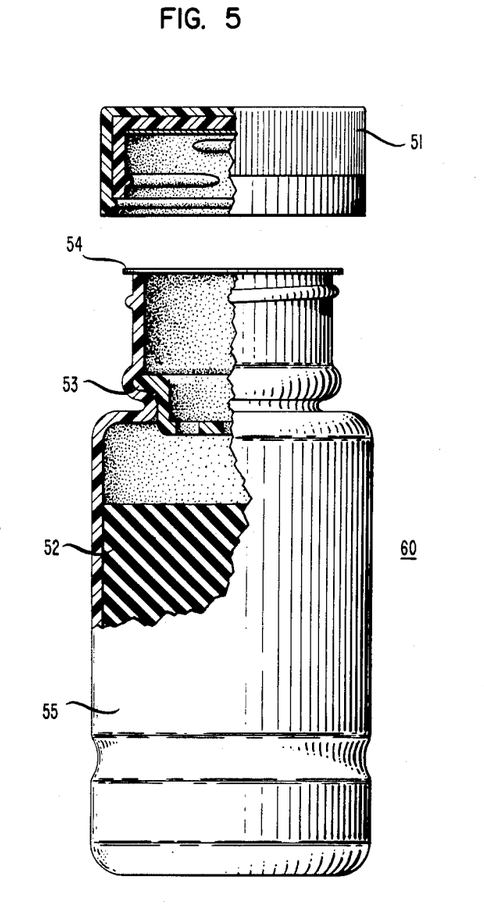
FIG. 5 shows a preferred embodiment of the invention in cross section.

FIG. 5 depicts an exemplary currently preferred article for sustained release of insecticide into the air surrounding the article. A plastic bottle 50, having a child-resistant cap 51, contains a quantity 52 of the above-described insecticide-containing elastomeric matrix. Inserted into the throat of the bottle is a perforated plastic member 53, to be referred to as a dermal barrier, that serves to prevent inadvertent skin contact with the insecticide-containing matrix while, at the same time, permitting passage of the insecticide into the air beyond the dermal barrier. Aluminum foil seal 54 serves to prevent release of insecticide into the air surrounding the article prior to activation of the article, and constitutes the means for activating the article. Activation is carried out by breaching or removal of the foil seal. The bottle has a constriction 55 which can be used to attach the bottle to a support structure by means of, e.g., a cable tie. Attachment preferably is such that water ingress into the bottle is prevented.

Figure 6:
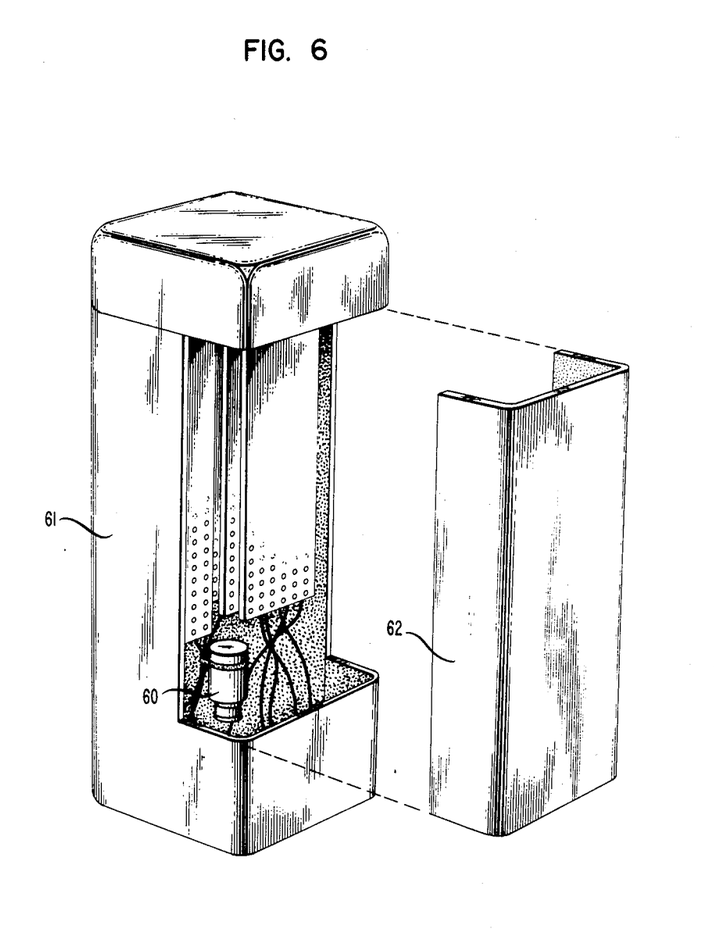
FIG. 6 schematically illustrates the preferred manner of use of the embodiment.

The above described preferred article can advantageously be used to control insect infestation of enclosures, typically enclosures used to protect outdoor utility equipment. Exemplary enclosures are pedestal-type closures and cabinets as used by communications, electric, gas, water, and cable TV companies. FIG. 6 schematically depicts an insecticide dispenser according to the invention 60 deployed in an exemplary enclosure 61. The depicted enclosure is of the pedestal type and is shown to contain communications (telephone) equipment. The dispenser is attached, in inverted position, to a cable. It will be understood that during normal operation the pedestal is closed by means of cover 62.

Exemplarily, the insecticide dispenser comprises a 4-ounce plastic bottle and about 90 g of insecticide-containing matrix of the previously described preferred type, with the concentration of insecticide in the matrix being about 20% by weight. The exemplary product has been found effective in controlling insect infestation in an enclosed volume up to about 4 cubic feet for, e.g., about a year. Insects against which the product has been found to be effective include ants, fire ants, bees, wasps, and cockroaches.

What is claimed is:

1. An article comprising:
   (a) a container;
   (b) an elastomeric matrix and at least one insecticide contained in the matrix, the matrix material having a modulus between about $10^4$ Pa and about $10^8$ Pa at 23° C. and a glass transition temperature $T_g$ less than 0° C., the matrix comprising polyurethane formed by a process comprising reacting a polyol with an isocyanate, the polyol consisting substantially of at least one member of the group consisting of hydroxyl-terminated polybutadiene and polyisoprene, the polyol having an average molecular weight in the range 400-10,000, and an average functionality in the range 2.0-3.0, the isocyanate consisting substantially of isocyanate selected from the group consisting of 4,4' diphenylmethane diisocyanate and the oligomers thereof, the isocyanate having an average molecular weight in the range 80-1000 and an average functionality between about 2 and about 3, the NCO/OH ratio of polyol and isocyanate being in the range of 0.8 to 1.2, the insecticide comprising 2,2' dichlorovinyl dimethyl phosphate, the insecticide-containing matrix being within the container;
   (c) means for activating the article; the article being adapted for substantially preventing, prior to activation of the article, release of the insecticide into the air surrounding the article, and for permitting, subsequent to activation of the article, sustained release of the insecticide into the air surrounding the article.

2. Article of claim 1, wherein the polyol consists substantially of hydroxyl-terminated polybutadiene, having an average molecular weight in the range 1000-4000, and an average functionality in the range 2.4-2.6, and wherein the matrix material has a modulus between $10^5$ and $10^7$ Pa.

3. Article of claim 2, comprising 10-30% insecticide and 70-90% polyurethane, the polyurethane formed from 5-15% isocyanate and 55-85% polyol, all percentages being weight percent of the total combination of matrix and insecticide contained therein.

4. Article of claim 3, further comprising a dermal barrier adapted for preventing inadvertent skin contact with the insecticide-containing matrix.

5. Article of claim 4, wherein the container is a plastic bottle with child-resistant screw top, the means for activating the article comprise a foil seal, and the dermal barrier comprises a perforated member inserted into the plastic bottle.

6. In combination,
   (a) an enclosure that is subject to insect infestation; and
   (b) one or more articles according to claim 1 contained within the enclosure; whereby the insect infestation of the enclosure is controlled.

7. Combination of claim 6, wherein the enclosure contains outdoor utility equipment of the type used for communications purposes, or for electric power, gas, or water supply purposes, or for purposes of provision of cable TV service.

* * * * *